United States Patent [19]

Lin et al.

[11] Patent Number: 4,699,786
[45] Date of Patent: Oct. 13, 1987

[54] ENHANCED LARGE SCALE CULTIVATION OF BORDETELLA PERTUSSIS CELLS FOR VACCINE PRODUCTION USING LACTOGLOBULIN

[75] Inventors: Wenlii Lin, New City; William A. Griffith, Monsey, both of N.Y.

[73] Assignee: American Cyanamid Company, Stamford, Conn.

[21] Appl. No.: 861,181

[22] Filed: May 9, 1986

[51] Int. Cl.$^4$ .................... C12N 1/20; A61K 39/02
[52] U.S. Cl. ...................................... 424/92; 435/253
[58] Field of Search ........................ 424/92; 435/253

[56] References Cited

U.S. PATENT DOCUMENTS 3,577,319  5/1971  Nielsen et al. .................. 435/253
4,429,046  1/1984  Lin et al. ........................ 424/92 X

OTHER PUBLICATIONS

Kirk–Othmer, Encyclopedia of Chemical Technology, vol. 13, 1969, p. 569.

Primary Examiner—Howard E. Schain
Attorney, Agent, or Firm—R. P. Raymond

[57] ABSTRACT

A *Bordetella pertussis* vaccine is prepared by deep tank cultivation using a seed grown in a biphasic culture system. An anion exchange resin in combination with β-lactoglobulin and a Modified Cohen-Wheeler or Modified Stainer-Schlolte medium is used in the process resulting in enhancement of the growth, antigen production and potency of the phase I *Bordetella pertussis* vaccine. An acellular *Bordetella pertussis* vaccine derived from the culture broth and cells of *Bordetella pertussis* useful in preparing an acellular vaccine and which are grown in a medium containing β-lactoglobulin and an anion exchange resin is also disclosed.

16 Claims, No Drawings

ENHANCED LARGE SCALE CULTIVATION OF BORDETELLA PERTUSSIS CELLS FOR VACCINE PRODUCTION USING LACTOGLOBULIN

SUMMARY OF THE INVENTION

The present invention relates to an improvement in the process of deep tank cultivation of *Bordetella pertussis* of U.S. Pat. Nos. 3,577,319 and 4,429,046, the teachings of which are incorporated herein by reference. More particularly, it concerns a process involving a combination of biphasic and liquid growth. The initial subcultures are conducted on biphasic blood agar. The organisms from this biphasic blood agar growth are transferred to a secondary biphasic culture consisting of Cohen-Wheeler (CW) or Stainer-Scholte (SS) liquid medium. After suitable growth, the liquid portion is used to inoculate Modified CW or Modified SS liquid medium containing an anion exchange resin such as Dowex ® 1-X8 or the like and an effective quantity of β-lactoglobulin in a larger vessel such as, for example, a 5-gallon vessel. After suitable growth, this liquid culture is used to innoculate Modified CW or Modified SS liquid medium containing anion exchange resin and β-lactoglobulin as hereinabove described in a larger, deep tank containing, for example, 125 gallons. After suitable growth in the tank, the organisms are killed, separated from the broth, and then suspended in buffered saline to produce the final vaccine. The supernatant may be saved for preparation of an acellular vaccine. This last step in the tank is the same as in the process formerly used.

Also, as in the former process, the operations are carried out as aseptically as possible. That is to say, the operations are aseptic as far as contamination with other organisms in concerned. As a result of the biphasic culturing and the incorporationn of purity checks, production yields are maximized.

DESCRIPTION OF THE PREFERRED EMBODIMENT

The incubated agars are inoculated and the organisms are grown at about 35°–37° C. Microscopic examination and purity checks follow all subculturing. The blood agar flasks containing 100 ml of Bordet-Gengou Agar plus 15-25% sheep or rabbit blood are overlaid with 25 ml of Modified CW medium having the following composition:

| INGREDIENT | GRAMS/LITER |
| --- | --- |
| Casamino Acids | 10 |
| Sodium Chloride | 2.5 |
| Potassium Phosphate Monobasic | 0.5 |
| Magnesium Chloride | 0.1 |
| Soluble Starch | 1.5 |
| Calcium Chloride | 0.01 |
| Ferrous Sulfate | 0.01 |
| Copper Sulfate | 0.005 |
| Glutathione | 0.025 |
| Yeast Extract Dialyzate | 75 |
| Distilled Water qs | 1000 ml | or 25 ml of Modified SS medium having the following composition:

| INGREDIENT | GRAMS/LITER |
| --- | --- |
| L-proline | 0.24 |
| Monosodium L-glutamate | 10.7 |
| Sodium Chloride | 2.5 |
| Potassium Chloride | 0.2 |
| Potassium Phosphate Monobasic | 0.5 |
| Magnesium Chloride | 0.1 |
| Calcium Chloride | 0.02 |
| Tris HCl Buffer, pH 7.6 0.05 $\underline{M}$ | 1.5 |
| Niacin | 0.004 |
| Glutathione | 0.1 |
| Ascorbic Acid | 0.02 |
| L-Cystine | 0.04 |
| Ferrous Sulfate.7H$_2$O | 0.01 |
| Distilled Water qs | 1000 ml |

The flasks are inoculated with 1–2 ml of cell suspension stock stored in liquid nitrogen, incubated at 35°–37° C. and continuously shaken at 60–80 strokes per minute. The incubation lasts for about 20–30 hours. Storage of the *B. pertussis* seed cells at liquid nitrogen temperatures are important to the results obtained.

The broth from the blood agar culture (2–5%) is transferred to a 5 liter toxin bottle containing 500 ml of CW charcoal agar overlaid with 200 ml of Modified CW medium, incubated at 35°–37° C. and continuously shaken at 60–80 strokes per minute. The incubation lasts for about 20–30 hours.

The broth from the CW charcoal culture (2–5%) is transferred to a bottle containing 3 liters of Modified CW or Modified SS medium with 3 g of Dowex ® 1-X8 resin or the like and with between 0.5 mg/ml and 6.0 mg/ml of β-lactoglobulin. This culture is incubated at 35°–37° C., while continuously being shaken at 60–80 strokes per minute. The incubation lasts for about 20–30 hours. The culture is used to innoculate a fermentation tank.

A fermentation tank containing approximately 300 liters of distilled water is sanitized for a minimum of one hour at 120°–123° C. Once cooled, it is drained, charged with 400 g of Dowex ® 1-X8 resin or the like, and 400 liters of the Modified CW or Modified SS medium is pumped into the tank and sterilized for 15–35 minutes at 120°–123° C. The tank is cooled to 32°–38°C. and held overnight under 10 lbs sterile air pressure. A sterile filtered solution of β-lactoglobulin is added to the tank medium to arrive at a final concentration of 0.5–6.0 mg/ml.

The culture from the liquid medium is inoculated into the fermentation tank and allowed to grow for about 20–48 hours at 32–38° C. with agitation and with approximately 3 cubic feet/minute of surface aeration.

After completion of fermentation, the tank is inactivated with a solution of sodium ethylmercurithiosalicylate to a final concentration of 0.01–0.02%. The contents of the vessel are cooled to about 20° C. and centrifuged at 15,000 rpm. The packed bacterial cells are collected and suspended in phosphate buffered saline, 0.85% solution containing 0.01% sodium ethylmercurithiosalicylate (thimerosol). The suspension is detoxified by allowing it to stand at 20°–25° C. for 2–10 days. Then, the stock is stored at 4° C. The supernatant, containing biologically active components, may be used for preparation of an acellular vaccine.

The main aspect of the present invention is concerned with a modification in the deep tank culture procedure which involves the addition of a substance such as β-lactoglobulin or the like, to a culture medium as described in U.S. Pat. No. 4,429,046 or to Modified SS medium as described herein. The addition of β-lactoglobulin has a significant effect on growth enhancement, antigen production and the vaccinal quality of the bacterium.

The culture method described in the above procedure, which includes the presence of β-lactoglobulin, is used to prepare a vaccine containing the hemagglutinating (HA) and lymohocytosis promoting (LPA) activities of B. pertussis. Hemagglutinin and lymphocytosis promoting factors are important components of the vaccine. The growth, hemagglutinin and lymphocytosis promoting activities of B. pertussis were greatly enhanced when the culture was prepared and tested as described below.

EXAMPLE 1

B. pertussis cells, grown on Bordet-Genou blood medium, were inoculated into 25 ml of Modified CW medium in a 500 ml flask and incubated in a water bath at 35° C. and 100 strokes per minute for 24 hours to prepare a seed culture. A 10% sterile filtered solution of β-lactoglobulin was added to 500 ml flasks containing 100 ml of Modified CW medium and 0.1 g of Dowex ® 1-X8 ion-exchange resin at a final concentration of either 0, 0.1, 0.2, 0.4 or 0.6 mg/ml. Each flask was inoculated with the seed to arrive at a final seed cencentration of 2 opacity units/ml as determined by comparing the opacity of the culture to a reference standard comprising plastic beads which was obtained from the U.S. Food and Drug Administration and which is specifically provided for such purpose. The flasks were then incubated at 35° C. and 100 strokes per minute.

Samples were removed from each flask at 24 hours and 48 hours and examined for opacity (OPU), determined as described above, and hemagglutinating (HA) and lyphocytosis promoting activities in the supernatant (LPA), determined according to techniques well known to those skilled in the art. The results of these examinations are shown in Table I.

TABLE I

Enhanced Growth and Production of Hemagglutinating and Lymphocytosis Promoting Activities in B. pertussis Culture Supernatant Due to β-lactoglobulin

| Amount of β-lacto-globulin added (mg/ml) | OPU/ml | | HA* (U/ml) | | LPA** (U/ml) | |
|---|---|---|---|---|---|---|
| | 24 hrs. | 48 hrs. | 24 hrs. | 48 hrs. | 24 hrs. | 48 hrs. |
| 0 | 23 | 23 | $2^1$ | 0 | 11 | 83 |
| 0.5 | 32 | 26 | $2^3$ | $2^2$ | 100 | 135 |
| 1.0 | 32 | 26 | $2^4$ | $2^2$ | 88 | 115 |
| 2.0 | 34 | 27 | $2^{4-5}$ | $2^{4-5}$ | 88 | 93 |
| 4.0 | 32 | 29 | $2^{4-5}$ | $2^4$ | 70 | 93 |
| 6.0 | 33 | 27 | $2^4$ | $2^4$ | 70 | 100 |

*Fresh goose red blood cells, 0.5% in saline, were used.
**Enzyme-linked immunosorbent assay (ELISA) with human haptoglobin was used.

Another procedure which discloses the beneficial aspects of adding β-lactoglobulin to a culture medium for B. pertussis is described in Example 2 below.

EXAMPLE 2

Two Woulfe bottles, each containing three liters of Modified CW medium with 0.3 g ion-exchange resin (Dowex ® 1-X8), were inoculated with a seed suspension of B. pertussis prepared as described in Example 1. A sterile filtered solution of β-lactoglobulin was added to one bottle at a final concentration of 1.0 mg/ml. Each bottle was incubated at 35° C. and shaken on a reciprocating shaker at 60 strokes per minute. Samples were removed at 24 and 48 hours. To assay for mouse potency*, culture samples were diluted to 20 OPU/ml for testing. Additional samples were centrifuged at 10,000 rpm for 30 minutes. The supernatants were saved for analysis of hemagglutinating activity. The data in Table II show that the addition of β-lactoglobulin to the culture medium significantly improves mouse potency and production of HA.

TABLE II

Improved Production of Hemagglutinating Activity and Mouse Potency* in B. pertussis Culture

| Amount of β-lactoglobulin added (mg/ml) | HA (U/ml) | | Mouse Potency* @ 20 OPU/ml (U/TID)** |
|---|---|---|---|
| | 24 hrs. | 48 hrs. | |
| 0 | $2^4$ | $2^2$ | 44 |
| 1 | $2^5$ | $2^5$ | 94 |

*According to the U.S. Code of Federal Regulations, 21 CFR 620.4 (a).
**Units per total immunizing dose.

Still another test was performed to corroborate the findings in Tables I and II. In this procedure a comparison was made between two different media, as described in Example 3.

EXAMPLE 3

Five hundred ml flasks, containing 100 ml of either Modified CW or Modified SS medium and 0.1 g ion-exchange resin (Dowex ® 1-X8), received a final concentration of 0 or 1.0 mg/ml β-lactoglobulin. Each flask was inoculated with a seed suspension B. pertussis prepared as noted in Example 1. The flasks were incubated at 35° C., 100 strokes per minute in a reciprocating water bath. Samples were removed at 24 and 48 hours and examined for opacity. Hemagglutinating and lymphocytosis promoting activities in the supernatant were assayed. In Table III, the results show that addition of β-lactoglobulin to either medium improved growth and the production of HA and LPA.

TABLE III

Enhanced Growth and Production of Hemagglutinating and Lymphocytosis Promoting Activities in B. pertussis Supernatant Using β-lactoglobulin and Different Media

| Media | β-lactoglobulin Concentration (mg/ml) | OPU/ml | | HA (U/ml) | | LPA (U/ml) | |
|---|---|---|---|---|---|---|---|
| | | 24 hrs. | 48 hrs. | 24 hrs. | 48 hrs. | 24 hrs. | 48 hrs. |
| CW | 0 | 29 | 23 | $2^{1-2}$ | $2^1$ | 22 | 46 |
| CW | 1.0 | 31 | 27 | $2^4$ | $2^{1-2}$ | 68 | 98 |
| SS | 0 | 26 | 33 | $2^{2-3}$ | $2^1$ | 69 | 75 |
| SS | 1.0 | 31 | 36 | $2^{4-5}$ | $2^3$ | 108 | 221 |

We claim:

1. A process for producing Pertussis Vaccine of high potency and low toxicity which comprises:

(a) culturing cells of *Bordetella pertussis* in a biphasic growth system comprising a liquid medium over blood agar;
(b) subculturing the cells in a biphasic growth system comprising a liquid medium over charcoal agar;
(c) subculturing the cells in a liquid medium with an anion exchange resin and β-lactoglobulin;
(d) subculturing the cells in a deep fermentation tank with a liquid medium with an anion exchange resin and β-lactoglobulin at about 32°–38° C.;
(e) killing the *Bordetella pertussis* cells and separating the killed cells from the broth.

2. The process according to claim 1 wherein the anion exchange resin is a basic anion exchange resin.

3. The process according to claim 2 wherein the β-lactoglobulin is at a final concentration of from about 0.5 to about 6.0 mg/ml.

4. A process according to claim 1, 2 or 3 which further comprises suspending the killed cells in isotonic saline.

5. A process according to claim 1, 2 or 3 which further comprises aseptically dispersing and suspending the killed cells in saline.

6. A process according to claim 1, 2 or 3 which further comprises using *Bordetella pertussis* cells that have been stored in liquid nitrogen to inoculate the biphasic growth system comprising a liquid medium over blood agar.

7. A process according to claim 4 which further comprises using *Bordetella pertussis* cells that have been stored in liquid nitrogen to inoculate the biphasic growth system comprising a liquid medium over blood agar.

8. A process according to claim 5 which further comprises using *Bordetella pertussis* cells that have been stored in liquid nitrogen to inoculate the biphasic growth system comprising a liquid medium over blood agar.

9. A *Bordetella pertussis* vaccine produced according to the process of claim 1.

10. A *Bordetella pertussis* vaccine produced according to the process of claim 6.

11. A *Bordetella pertussis* vaccine produced according to the process of claim 7.

12. A *Bordetella pertussis* vaccine produced according to the process of claim 8.

13. An acellular *Bordetella pertussis* vaccine which comprises the broth produced according to the process of claim 1, 2 or 3.

14. An acellular *Bordetella pertussis* vaccine which comprises the broth produced according to the process of claim 6.

15. A composition of matter useful in preparing an acellular *Bordetella pertussis* vaccine which comprises cells of *Bordetella pertussis* produced according to the process of claim 1, 2 or 3.

16. A composition of matter useful in preparing an acellular *Bordetella pertussis* vaccine which comprises cells of *Bordetella pertussis* produced according to the process of claim 6.

* * * * *